United States Patent

Bayly et al.

[11] 4,202,976
[45] May 13, 1980

[54] SELENIUM-75 LABELLED DERIVATIVES OF FOLATES

[76] Inventors: Russell J. Bayly; Virginia E. M. Chambers; Reginald Monks, all of c/o The Radiochemical Centre, Amersham, Buckinghamshire, England

[21] Appl. No.: 853,565

[22] Filed: Nov. 21, 1977

Related U.S. Application Data

[63] Continuation-in-part of Ser. No. 531,748, Dec. 11, 1974, Pat. No. 4,115,065.

[30] Foreign Application Priority Data

Sep. 11, 1973 [GB] United Kingdom .............. 57433/73.

[51] Int. Cl.² .......................................... C07D 475/04
[52] U.S. Cl. ...................................... 544/261; 544/258
[58] Field of Search .................................. 544/261, 258

[56] References Cited

U.S. PATENT DOCUMENTS

| | | | |
|---|---|---|---|
| 3,988,431 | 10/1976 | Givas et al. | 23/230 B |
| 3,993,741 | 11/1976 | Otto | 23/230 B |
| 4,038,033 | 7/1977 | Monks et al. | 536/23 |

*Primary Examiner*—Paul M. Coughlan, Jr.

[57] ABSTRACT

Novel selenium-75 derivatives of folates, which are useful in competitive radio assay of folates, have the general formula:

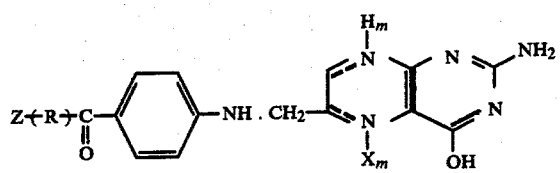

where a dotted bond line indicates that the bond may be single or double, and where
X is H or —CH₃,
m is 0 or 1 (such that the adjacent nitrogen atom is trivalent), and either
(a) R is

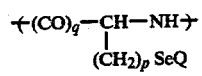

and is attached through the nitrogen atom to the pteroyl residue where
q is 0 or 1
p is 1 or 2
Q is $C_xH_{2x+1}$ where x is from 1 to 6
and when q is 0, Z is H and when q is 1, Z is HO, or
(b) R is

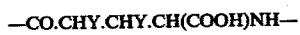

and is attached through the nitrogen atom to the pteroyl residue, where Z is HO,
one group Y is —H and the other group Y is —SeC$_x$H$_{2x+1}$ where x is from 1 to 6 and esters and salts of such acid.

6 Claims, No Drawings

SELENIUM-75 LABELLED DERIVATIVES OF FOLATES

This invention relates to novel selenium labelled derivatives of folate compounds. Our co-pending application Ser. No. 531,748, filed Dec. 11, 1974, now U.S. Pat. No. 4,115,065, of which this is a continuation-in-part, describes and claims the use of these derivatives in the saturation analysis of folate compounds by competitive radioassay.

Folic acid has the formula (I)

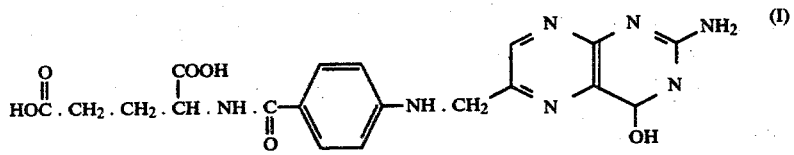

Naturally occurring folic acid is invariably in a mixture with other related compounds, and it is this naturally occurring mixture which is referred to herein as folate compounds. The other related compounds may have the formula (II)

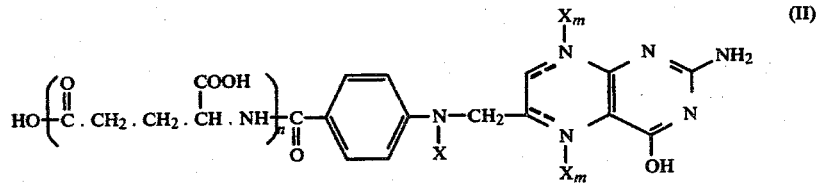

where a dotted second bond line indicates that the bond may be single or double, and where X may be the same or different at different locations in the molecule and is in each case H, $-CH_3$, $-CHO$, or $-CH_2OH$ m may be the same or different at different locations in the molecule and is in each case 0 or 1 (such that the adjacent nitrogen atom is always trivalent) and n is from 1 to 13.

Alternatively, the groups X attached to the nitrogen atoms in the 5- and 10-positions may be absent and replaced by a methylene or methenyl bridge. The term folate compounds covers esters and salts of the above acids.

In the practice of saturation analysis using radioactive labelled compounds an essential ingredient is a labelled version of the substance to be measured which competes for binding sites in a quantitatively definable manner with the native substance, and which can readily be counted after an appropriate separation procedure. The compounds it is desired to measure are typically organic compounds present in small or very small amounts in body fluids or tissues. These compounds frequently contain at the most only the elements carbon, hydrogen, oxygen, nitrogen, phosphorus and sulphur. This introduces a severe limitation on the range of radionuclides available for labelling. C14 is the only practical isotope of carbon which can be used, and tritium the only radioactive isotope of hydrogen. Neither oxygen or nitrogen have radioactive isotopes with half-lives in excess of 10 minutes. Phosphorus and sulphur are less commonly found in the compounds of interest, but even then the only practical radionuclides are P32, a pure Beta emitter with a half-life of approximately 14 days, and S35, another pure β-emitter with a half-life of approximately 87 days. Carbon-14 is another pure β-emitter and has the additional disadvantage for many applications of a low specific activity because of its very long half-life, and tritium has only a very weak β-emission. In summary, not one of these elements has a usable γ-emitting isotope, and the β-emitters have various disadvantages.

This has led to the use of labelling with "foreign" nuclides for which the requirements are:

(i) It must have a "suitable" half-life; if too short it is impracticable to use and if too long, it will have a low specific radioactivity even when nuclidically pure.

(ii) It should emit γ-radiation of a suitable energy. The counting of γ-emitters is more rapid and more economical than that of β-emitters.

(iii) It should be economically available at an adequate specific radioactivity.

(iv) It should be capable of stable incorporation in a range of compounds.

(v) It should produce the minimum distortion to the molecule in which it is introduced.

Virtually the only γ-emitting nuclides used in radioactive saturation analysis to date, have been the two iodine isotopes, I125 and I131. When measured against the criteria outlined above, it is apparent that the iodine isotopes are acceptable though with some limitations: the 8-day half-life of I131 is too short for many purposes and even the 60 days for I125 is sometimes undesirably short. I125 has soft γ-radiation and X-rays which can be adsorbed in a fashion which limits its ease of counting. Se75 has certain advantages over the more commonly used iodine isotope, I125. It has a longer half-life (120 days) and a more energetic γ-emission which will facilitate counting. It can be readily prepared by neutron irradiation of enriched Se74 at specific radioactivities which are adequate for many purposes; if higher specific activities are needed the bombardment of As75 with protons in a cyclotron yields essentially carrier-free Se75.

Levels of folates in biological samples may be determined by methods of saturation analysis employing tritiated folic acid as the radioactive ligand. The use of gamma-emitting isotopes to label the radioactive ligand would appear feasible for iodine-125 and selenium-75. Although iodine can be introduced into the p-aminobenzoate moiety of folates, the product is unsuitable for saturation analysis of folates. The radioiodinated material cannot be produced at sufficiently high specific activity and does not compete adequately with natural folates for the binding proteins used in saturation analysis of folates. Alternative approaches to introducing iodine-125 into folates involve the replacement of the L-glutamate residue of folates by a radioiodinated species such as iodotyramine-I125 or iodotyrosine-I125. This replacement may be effected by coupling either iodotyramine-I125, or iodotyrosine-I125 or one of its esters, to pteroic acid or a derivative of pteroic acid, or alternatively, by radioiodinating an inactive conjugate of pteroic acid and a moiety such as tyramine or tyrosine. Labelling of folates could also be effected by coupling either iodotyramine-I125 or iodotyrosine-I125 directly for example to folic acid to form pteroyl-L-glutamyl-iodotyrosine-I125.

In the case of selenium-75 labelling the possibility arises of replacing the p-aminobenzoyl moiety with a selenophene derivative or displacing a 4-tosyl group with a selenium containing nucleophile, e.g. SeCN$^-$, H Se$^-$, or CH$_3$Se$^-$. The former case would involve some intricate synthetic chemistry whilst in the latter case a determinant group in the binding of folate to proteins, viz. the pteridine group, would be modified. However, the introduction of selenium-75 into the folate molecule can be accomplished likewise to the introduction of iodine-125 by replacing the L-glutamate residue of folates with a selenium-75 labelled selenoamine or selenoamino-acid, e.g. selenomethionine-Se75, methyl-selenocysteine-Se75, or 2-(methylseleno)-ethylamine-Se75. This replacement may be effected similarly by coupling one of these seleno-amines or amino-acids to pteroic acid or a derivative of pteroic acid. Alternatively, the halogen atom of a conjugate formed from pteroic acid and a halogen-substituted amino-acid, such as β-chloroalanine or β- or γ-chloroglutamic acid, could be substituted with a selenium-75 containing nucleophile, e.g. CH$_3$Se$^-$. Labelling of folates with selenium-75 could also be effected by coupling, for example, selenomethionine-Se75 directly to folic acid to form pteroyl-L-glutanoyl-selenomethionine-Se75.

One advantage of labelling with selenium over labelling with iodine is that modifications to the steric configuration of the folic acid molecule may be more limited. The binding of the radioactive ligand to a protein may therefore more closely resemble the binding of the natural folic acid.

The preparation of amino-acid analogues of folate for the study of enzyme systems has been previously described, e.g. in The Journal of Biological Chemistry, Volume 242, No. 7, (Apr. 10, 1967) pages 1466-76. The methods used for these syntheses are well-known in the art, consisting of the reaction of isobutyl chloroformate with a N$^{10}$-protected pteroic acid in the presence of a tertiary amine, the reaction being carried out under anhydrous conditions in dry solvents such as dioxan and dimethylformamide in order to form the mixed anhydride. The mixed anhydride is subsequently reacted with the required amino-acid ester in aqueous organic media to form an amino-acid conjugate of pteroic acid. If these reactions are applied to a range of selenium-75 labelled amines or amino-acids, e.g. selenomethionine, selenoethionine, Se-methyl-selenocysteine, Se-ethyl-selenocysteine, 2-(methylseleno)-ethylamine, then a range of selenium-75 labelled amino-acid analogues of folic acid may be prepared which can find use as radioactive ligands in the saturation analysis of folate.

The invention provides compounds having the formula (III)

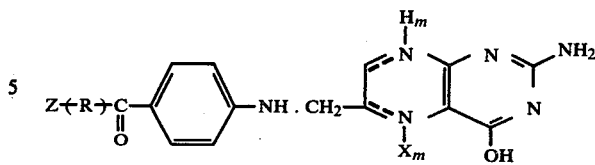

where a dotted bond line indicates that the bond may be single or double, and where
 X is H or —CH$_3$,
 m is 0 or 1 (such that the adjacent nitrogen atom is trivalent), and either
(a) R is

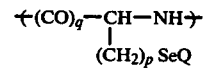

and is attached through the nitrogen atom to the pteroyl residue where
 q is 0 or 1
 p is 1 or 2
 Q is C$_x$H$_{2x+1}$ where x is from 1 to 6
and when q is 0, Z is H, and when q is 1, Z is HO, or
(b) R is —CO.CHY.CHY.CH(COOH)NH— and is attached through the nitrogen atom to the pteroyl residue, where Z is HO,
 one group Y is —H
 and the other group Y is —SeC$_x$H$_{2x+1}$ where x is from 1 to 6 or an ester or salt of such acid.

These compounds are selenium-75-labelled versions of folate compounds, including selenium-75-labelled versions of folic acid itself, and are accordingly suitable for use in the saturation analysis of folate compounds including folic acid.

The following Examples illustrate the invention,

EXAMPLE 1

Preparation of Se-methyl-L-selenocysteine-Se75

Sodium (24 mg; 1.05 m atom) was added to a reaction vessel containing red selenium-Se75 (78.5 mg; 1.0 m atom, 295 mCi) suspended in 20 ml of liquid ammonia, the reaction vessel being connected to a vacuum manifold and vented to the atmosphere via a Carbasorb/charcoal trap. The reaction mixture was stirred until a red-brown solution of disodium diselenide was obtained. β-chloro-L-alanine, sodium salt (205 mg; 1.41 m mol) was then added to the solution and stirring was continued until the ammonia had evaporated. The residue of crude selenocystine-Se75 was carefully dissolved in 2 molar hydrochloric acid and a precipitate of red selenium was removed by centrifugation. The pH of the supernate was adjusted to 6–7 with 4 molar ammonium hydroxide. The yellow precipiate which deposited was separated, washed with water (1 ml) and ethanol (3 ml), and dried in vacuo to yield L-selenocystineSe75 (136 mg; 0.407 m mol; 236 mCi).

L-selenocystine-Se75 (100 mg; 0.3 m mol; 172 mCi) was transferred to a reaction vessel into which 20 ml of liquid ammonia was condensed. Sodium (32.9 mg; 1.43 m atom) was added to the reaction vessel, and after reaction had taken place, methyl iodide (125 μl; 2 m mol) was added to the stirred solution causing the blue coloration to be discharged. After a further 10 minutes reaction, ammonium iodide (164 mg; 1.13 m mol) was added and the ammonia then allowed to evaporate. The residue was dissolved in water (1 ml) and reprecipitated with acetone (8 ml). The product was separated, redissolved in water (1 ml), and reprecipitated with ethanol (2 ml). After cooling the aqueous-alcoholic solution for 1 hour the product was separated by centrifugation, washed with ethanol (1 ml), and dried in vacuo to yield Se-methyl-L-selenocysteine-Se75 (25 mg; 0.15 m mol; 44 mCi).

Preparation of N-Pteroyl-Se-methyl-L-selenocysteine-Se75

Isobutyl chloroformate (13.5 μl) and thiethylamine (13.5 μl) were added under anhydrous conditions to $N^{10}$-trifluoroacetylpteroic acid (22 mg; vacuum dried) in dry dimethylformamide (0.5 ml) at 5° C. The mixture was allowed to react under nitrogen and attain room temperature over a period of 30 minutes in order to form the mixed anhyride. A further 2 ml of dimethylformamide was added to the reaction mixture followed by the addition of Se-methyl-L-selenocysteine-Se75, sodium salt (14 mg; 18.4 mCi) in water (1.5 ml). The reaction mixture was stirred overnight at room temperature and then left for a further 24 hours. It was then lyophilized and the residue was heated at 60° C. for 30 minutes with 0.1 molar sodium hydroxide (3 ml) in order to remove the trifluoroacetyl group; the hydrolysis was conducted in darkness under an atmosphere of nitrogen. The solution was cooled and adjusted to pH 3.0 with dilute hydrochloric acid, whereupon a precipitate formed. The precipitate was separated by centrifugation, washed with water (2 ml), and after dissolving in dilute ammonium hydroxide solution (0.25 ml of 0.05 M), was purified by thin layer chromatography (Avicel F 1 mm cellulose; Eluent: 5% aqueous ammonium bicarbonate). The chromatography was conduced in darkness. The plate was autoradiographed and the component at Rf approx. 0.19 was removed and extracted into 0.1 molar ammonium hydroxide to give 2.5 mCi of a solution of N-Pteroyl-Se-methyl-L-selenocysteine-Se75, λ max 259, 286 nm (pH 11.0 phosphate buffer).

EXAMPLE 2

Preparation of N-Pteroyl-L-selenomethionine-Se75

Isobutyl chloroformate (13.5 μl) and triethylamine (13.5μ) were added under anhydrous conditions to $N^{10}$-trifluoroacetylpteroic acid (22 mg; vacuum dried) in dry dimethylformamide (1 ml) at 5° C. The mixture was allowed to react under nitrogen and attain room temperature over a period of 30 minutes in order to form the mixed anhydride. A further 2 ml of dimethylformamide was added to the reaction mixture followed by the addition of L-selenomethionine-Se75, sodium salt (3.5 mg; 20 mCi) in water (1 ml). The reaction mixture was stirred overnight at room temperature. It was then lyophilized and the residue was heated at 60° C. for 40 minutes with 0.1 molar sodium hydroxide (3 ml) in order to remove the trifluoroacetyl group; the hydrolysis was conducted in darkness under an atmosphere of nitrogen. A small yellow precipitate which formed was redissolved by the addition of 0.1 molar sodium hydroxide. The solution was cooled to approximately 5° C. and adjusted to pH 3.0 with dilute hydrochloric acid, whereupon a yellow precipitate formed. The precipitate was separated by centrifugation, washed with water (2 ml) and then stirred for 10 minutes with 1.0 molar ammonium hydroxide (2 ml). The remaining yellow solid was separated, washed with water (2 ml), and dried in vacuo to yield 1.75 mCi of N-Pteroyl-L-selenomethionine-Se75, λ max 259, 281 nm (pH 11.0 phosphate buffer).

EXAMPLE 3

Preparation of 2-(methylseleno)-ethylamine-Se75

Sodium (9.2 mg; 0.4 m atom) was added to a reaction vessel containing red selenium-Se75 (28.8 mg; 0.366 m atom; 3.8 mCi) in 25 ml of liquid ammonia, the reaction vessel being connected to a vacuum manifold and vented to the atmosphere via a Carbasorb/charcoal trap. The reaction mixture was stirred for approximately 10 minutes until a brown solution of disodium diselenide was obtained. Methyl iodide (65.2 mg; 0.46 m mol) was added to the stirred solution to give a colorless solution of dimethyl diselenide. After approximately 3 minutes a further quantity of sodium (11 mg) was added to the reaction vessel until a permanent blue-black coloration was obtained, indicating complete cleavage of the diselenide bond with formation of sodium methyl selenide. 2-bromoethylamine hydrobromide (83 mg; 0.4 m mol) was added to the reaction mixture which was then stirred until all the ammonia had evaporated. The residue was dried in vacuo, dissolved in ethanol, and purified by preparative thin layer chromatography (Avicel F 1 mm cellulose. Eluent: butanol, water, acetic acid (15:25:60)). The plate was autoradiographed and the major component, corresponding on an analytical plate to the fastest running component with Rf 0.81, was removed and extracted into ethanol to give 1.4 mCi of 2-methylseleno)-ethylamine-Se75.

Coupling of $N^{10}$-Trifluoroacetylpteroic acid with 2-(methylseleno)-ethylamine-Se75

Isobutyl chloroformate (11 μl) and triethylamine (10 μl) were added under anhydrous conditions to $N^{10}$-trifluoroacetylpteroic acid (20 mg; 0.049 m mol; vacuum dried) in dry dimethylformamide (0.4 ml) at 10° C. The solution was stirred at room temperature for 45 minutes. Further triethylamine (20 μl) was then added and the solution was transferred to a flask containing 2-(methylseleno)-ethylamine-Se75 (16 mg; 0.12 m mol; 1.2 mCi). The reaction mixture was stirred overnight at room temperature and was then subjected to thin layer chromotography (Merck Kieselgel 60F₂₅₄. Eluent: methanol). The required product was located by autoradiogrphy and UV fluorescence. The component at Rf 0.63 was removed and extracted into methanol to give 120 μCi of a methanolic solution of the 2-(methylseleno)-ethylamine-Se75 conjugate of $N^{10}$-Trifluoroacetylpteroic acid, λ max 257, 286 nm (pH 11.0 phosphate buffer). This product can be converted to N-pteroyl-2-(methylseleno)-ethylamine-Se75 by the hydrolysis technique generally described in Examples 1 and 2.

We claim:

1. A compound having the general formula (III)

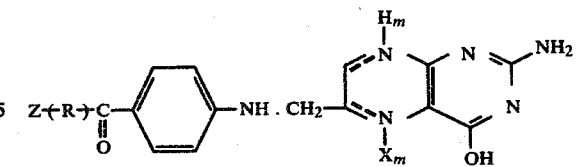

where a dotted bond line indicates that the bond may be single or double, and where X is H or —CH$_3$, m is 0 or 1 (such that the adjacent nitrogen atom is trivalent), and either (a) R is

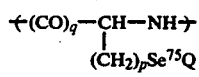

and is attached through the nitrogen atom to the pteroyl residue where q is 0 or 1 p is 1 or 2

Q is $C_xH_{2x+1}$ where x is from 1 to 6 and when q is 0, Z is H and when q is 1, Z is HO, or (b) R is

and is attached through the nitrogen atom to the pteroyl residue, where Z is HO, one group Y is —H and the other group Y is —Se$^{75}$ $C_xH_{2x+1}$ where x is from 1 to 6 or an ester or salt of such acid.

2. N-Pteroyl-Se-methyl-L-selenocysteine-Se75.

3. N-Pteroyl-L-selenomethionine-Se75.

4. N-Pteroyl-2-(methylseleno)-ethylamine-Se75.

5. A compound according to claim 1 wherein R is as defined in (a) and x is 1.

6. A compound according to claim 1 wherein R is as defined in (b) and x is 1.

* * * * *